(12) United States Patent
Borody

(10) Patent No.: US 7,241,741 B2
(45) Date of Patent: *Jul. 10, 2007

(54) METHODS AND COMPOSITIONS FOR THE TREATMENT OF ASTHMA AND RELATED DISORDERS

(75) Inventor: Thomas J. Borody, New South Wales (AU)

(73) Assignee: Atopic Pty. Ltd. (AU)

( * ) Notice: Subject to any disclaimer, the term of this patent is extended or adjusted under 35 U.S.C. 154(b) by 0 days.

This patent is subject to a terminal disclaimer.

(21) Appl. No.: 10/897,714

(22) Filed: Jul. 23, 2004

(65) Prior Publication Data

US 2005/0054588 A1    Mar. 10, 2005

Related U.S. Application Data

(63) Continuation of application No. PCT/AU03/00074, filed on Jan. 24, 2003.

(30) Foreign Application Priority Data

Jan. 25, 2002    (AU) .................... PS0177

(51) Int. Cl.
*A61K 31/04* (2006.01)
*A61K 31/44* (2006.01)
*A61K 31/47* (2006.01)
*A61K 31/65* (2006.01)
*A61K 31/71* (2006.01)

(52) U.S. Cl. ............... 514/29; 514/31; 514/152; 514/192; 514/282; 514/311; 514/393; 514/394; 514/462; 514/560; 514/741; 514/836

(58) Field of Classification Search ............ 514/29, 514/31, 152, 192, 282, 311, 393, 394, 462, 514/560, 741, 826

See application file for complete search history.

(56) References Cited

U.S. PATENT DOCUMENTS

| 6,291,500 B2 * | 9/2001 | Ponikau ............. 514/393 |
| 6,503,953 B2 * | 1/2003 | Vyden ............. 514/741 |
| 2001/0038825 A1 | 11/2001 | Hite |
| 2005/0124561 A1 | 6/2005 | Ponikau |

FOREIGN PATENT DOCUMENTS

WO    WO 02/07682 A1    1/2002

OTHER PUBLICATIONS

Yoshida, M. et al., "Treatment of Severe Pneumonia Due to Methicillin-Resistant Staphylococcus Aureus (MRSA) and Candida Krusei with Granulocyte Colony-Stimulating Factor (G-CSF): A Case Report," Second Department of Internal Medicine, Aug. 1993, vol. 67(8), abstract only.

Nakagawa, Y., et al., "A Case of Secondary Invasive Pulmonary Aspergillosis Originiating From an Aspergilloma, Successfully Treated With Itraconazole," Mar. 1998, vol. 36(3), abstract only.

* cited by examiner

*Primary Examiner*—Elli Peselev
(74) *Attorney, Agent, or Firm*—Alston & Bird LLP

(57) ABSTRACT

The present invention provides methods for the treatment of respiratory tract mucositis in individuals in need of such treatment, the method comprising the systemic administration to the individual of therapeutically effective amounts of at least one anti-fungal agent and at least one anti-bacterial agent, wherein the treatment does not involve the cessation of use of emollients by the individual. The present invention also provides compositions suitable for use in the treatment of respiratory tract mucositis.

18 Claims, No Drawings

METHODS AND COMPOSITIONS FOR THE TREATMENT OF ASTHMA AND RELATED DISORDERS

CROSS-REFERENCE RELATED APPLICATIONS

This application is a continuation application of PCT/AU03/00074 filed on Jan. 24, 2003, which claims priority to Australian Application No. PS0177, filed on Jan. 25, 2002, both of which are incorporated herein by reference in their entirety.

FIELD OF THE INVENTION

This invention relates to methods for the treatment of mucositis including asthma and related disorders such as chronic bronchitis and sinusitis, and to pharmaceutical compositions for use in such treatment.

BACKGROUND OF THE INVENTION

Mucositis refers to inflammation of the mucous membranes caused by an infection. In the respiratory tract, mucositis affects not only the nose, sinuses and the large airways but also the small airways of the lungs. Mucositis of the nose and sinuses is called chronic rhinosinusitis. In the smaller airways it is termed asthma.

Asthma is a common disorder causing marked morbidity and significant mortality. The incidence of asthma in the United States and other Western countries is over 5% and growing. In the US alone asthma affects approximately 17 million people and accounts for nearly half a million hospital admissions each year.

In general the cause of chronic mucositis in the respiratory tract is not known. However, in a percentage of patients, superficial or non-invasive fungal organisms appear to be present within the mucus. It appears that respiratory tract mucositis is caused, at least in part, by a chronic fungal infection.

Typically, mucositis may be treated with surgery, steroid therapy or anti-inflammatory agents. However such therapies fail to address the infection components of the mucositis.

Alternatively treatment may include mucosal administration of an anti-fungal agent. U.S. Pat. No. 6,291,500 (Ponikau) describes the treatment of non-invasive fungus-induced mucositis by mucosal administration of a formulation including an anti-fungal agent. According to Ponikau, the formulation may also include an antibiotic.

The Applicant has noted that although such mucosal administration can reduce symptoms of mucositis, suppress severity or reduce relapses of the condition if administered for a long period of time, this type of therapy of an anti-fungal agent administered superficially to the mucosa suffers from the disadvantage that it does not address the invasive component of the fungal infection. Indeed mucosal administration has the potential to lead to the development of resistant fungi where only a small amount of the anti-fungal agent reaches the fungi inhabiting the deeper layers of mucosal membranes allowing them to multiply at low levels of anti-fungal exposure, thereby exacerbating the underlying problem.

WO 02/07682 (Vyden) describes the treatment of atopic disorders, including asthma, using an anti-fungal agent and an antibiotic, wherein the treatment also requires the reduction or cessation of use of emollients by the patient.

The Applicant has surprisingly found, however, that such reduction or cessation of emollient use is in fact often unnecessary, and effective treatment of asthma and other respiratory tract mucositis can be achieved using at least one anti-fungal agent and at least one anti-bacterial agent without need for a reduction or cessation of use of emollients.

It is an object of the present invention to provide an effective treatment for respiratory tract mucositis which overcomes or at least substantially ameliorates the shortcomings of the prior art.

SUMMARY OF THE INVENTION

According to a first aspect of the present invention there is provided a method for the treatment of respiratory tract mucositis in an individual in need of such treatment, the method comprising the systemic administration to the individual of therapeutically effective amounts of at least one anti-fungal agent and at least one anti-bacterial agent, wherein the treatment does not involve the cessation of use of emollients by the individual.

According to a second aspect of the present invention there is provided a method for the treatment of respiratory tract mucositis in an individual in need of such treatment, the method comprising the systemic administration to the individual of therapeutically effective amounts of at least one anti-fungal agent and two or more anti-bacterial agents. Typically, there are administered one anti-fungal agent and two anti-bacterial agents. Optionally, the treatment may further include the reduction or cessation of the use of emollients by the individual.

Typically the at least one anti-fungal agent is selected from the group consisting of: amphotericin B, flucytosine, ketoconazole, miconazole, itraconazole, fluconazole, griseofulvin, clotrimazole, econazole, terconazole, butoconazole, oxiconazole, sulconazole, supraconazole, voriconazole, ciclopirox olamine, haloprogin, tolnaftate, naftifine, terbinafine hydrochloride, morpholines, nystatin, natamycin, butenafine, undecylenic acid, proprionic acid and caprylic acid.

More typically the at least one anti-fungal agent is selected from the sub-group consisting of: amphotericin B; ketoconazole; fluconazole; and terbinafine hydrochloride.

Typically the at least one anti-bacterial agent belongs to one or more of the following classes: tetracyclines, penicillins, macrolides, quinolones, chloramphenicol, rifamycins, sulphonamides, co-trimoxazole, and oxazolidinones.

More typically the at least one anti-bacterial agent is a tetracycline, a macrolide or a rifamycin.

Most typically the at least one anti-bacterial agent is selected from the group consisting of: doxycycline, chlortetracycline, tetracycline hydrochloride, oxytetracycline, demeclocycline, methacycline, minocycline, penicillin, amoxycillin, erythromycin, clarithromycin, roxithromycin, azithromycin, spiramycin, oleandomycin, josamycin, kitsamysin, flurithromycin, nalidixic acid, oxolinic acid, norfloxacin, perfloxacin, amifloxacin, ofloxacin, ciprofloxacin, sparfloxacin, levofloxacin, rifabutin, rifampicin, rifapentin, sulfisoxazole, sulfamethoxazole, sulfadiazine, sulfadoxine, sulfasalazine, sulfaphenazole, dapsone, sulfacytidine, and linezolid.

The at least one anti-fungal agent and at least one anti-bacterial agent may be administered sequentially, or simultaneously.

In a preferred embodiment of the method of the invention there is administered to an individual a pharmaceutical composition comprising one anti-fungal agent selected from the above-mentioned group combined with two or more anti-bacterial agents selected from the group consisting of: doxycycline, chlortetracycline, tetracycline hydrochloride, oxytetracycline, demeclocycline, methacycline, minocycline, penicillin, amoxycillin, erythromycin, clarithromycin, roxithromycin, azithromycin, spiramycin, oleandomycin, josamycin, kitsamysin, flurithromycin, nalidixic acid, oxolinic acid, norfloxacin, perfloxacin, amifloxacin, ofloxacin, ciprofloxacin, sparfloxacin, levofloxacin, rifabutin, rifampicin, rifapentin, sulfisoxazole, sulfamethoxazole, sulfadiazine, sulfadoxine, sulfasalazine, sulfaphenazole, dapsone, sulfacytidine, and linezolid.

In a particularly preferred embodiment there is administered to an individual a pharmaceutical composition comprising the anti-fungal agent terbinafine hydrochloride and the anti-bacterial agents doxycycline and rifabutin.

In a particularly preferred embodiment there is administered to an individual a pharmaceutical composition comprising the anti-fungal agent terbinafine hydrochloride and the anti-bacterial agents clarithromycin and rifampicin.

In a particularly preferred embodiment there is administered to an individual a pharmaceutical composition comprising the anti-fungal agent terbinafine hydrochloride and the anti-bacterial agents doxycycline and rifampicin.

In a particularly preferred embodiment there is administered to an individual a pharmaceutical composition comprising the anti-fungal agent terbinafine hydrochloride and the anti-bacterial agents clarithromycin and rifabutin.

In a particularly preferred embodiment there is administered to an individual a pharmaceutical composition comprising the anti-fungal agent terbinafine hydrochloride and the anti-bacterial agents tetracycline hydrochloride and rifampicin.

In a particularly preferred embodiment there is administered to an individual a pharmaceutical composition comprising the anti-fungal agent fluconazole and the anti-bacterial agents clarithromycin and rifabutin.

In a particularly preferred embodiment there is administered to an individual a pharmaceutical composition comprising the anti-fungal agent fluconazole and the anti-bacterial agents azithromycin and rifampicin.

In a particularly preferred embodiment there is administered to an individual a pharmaceutical composition comprising the anti-fungal agent terbinafine hydrochloride and the anti-bacterial agents azithromycin and rifabutin.

In a particularly preferred embodiment there is administered to an individual a pharmaceutical composition comprising the anti-fungal agent terbinafine hydrochloride and the anti-bacterial agents erythromycin and amoxycillin.

In a particularly preferred embodiment there is administered to an individual a pharmaceutical composition comprising the anti-fungal agent terbinafine hydrochloride and the anti-bacterial agents clarithromycin and doxycycline.

Typically, systemic administration may further include one or more of the following: a mucolytic agent, a steroid, a decongestant and/or a bronchodilator.

According to a third aspect of the present invention there is provided a pharmaceutical composition for systemic administration for the treatment of respiratory tract mucositis, the composition comprising therapeutically effective amounts of at least one anti-fungal agent and two or more anti-bacterial agents.

In a preferred embodiment of the pharmaceutical composition of the invention the composition includes one antifungal agent selected from the above-mentioned group combined with two or more anti-bacterial agents selected from the group consisting of doxycycline, chlortetracycline, tetracycline hydrochloride, oxytetracycline, demeclocycline, methacycline, minocycline, penicillin, amoxycillin, erythromycin, clarithromycin, roxithromycin, azithromycin, spiramycin, oleandomycin, josamycin, kitsamysin, flurithromycin, nalidixic acid, oxolinic acid, norfloxacin, perfloxacin, amifloxacin, ofloxacin, ciprofloxacin, sparfloxacin, levofloxacin, rifabutin, rifampicin, rifapentin, sulfisoxazole, sulfamethoxazole, sulfadiazine, sulfadoxine, sulfasalazine, sulfaphenazole, dapsone, sulfacytidine, and linezolid.

In a particular embodiment the composition comprises the anti-fungal agent terbinafine hydrochloride and the anti-bacterial agents doxycycline and rifabutin.

In a particular embodiment the composition comprises the anti-fungal agent terbinafine hydrochloride and the anti-bacterial agents clarithromycin and rifampicin.

In a particular embodiment the composition comprises the anti-fungal agent terbinafine hydrochloride and the anti-bacterial agents doxycycline and rifampicin.

In a particular embodiment the composition comprises the anti-fungal agent terbinafine hydrochloride and the anti-bacterial agents clarithromycin and rifabutin.

In a particular embodiment the composition comprises the anti-fungal agent terbinafine hydrochloride and the anti-bacterial agents tetracycline hydrochloride and rifampicin.

In a particular embodiment the composition comprises the anti-fungal agent fluconazole and the anti-bacterial agents clarithromycin and rifabutin.

In a particular embodiment the composition comprises the anti-fungal agent fluconazole and the anti-bacterial agents azithromycin and rifampicin.

In a particular embodiment the composition comprises the anti-fungal agent terbinafine hydrochloride and the anti-bacterial agents azithromycin and rifabutin.

In a particular embodiment the composition comprises the anti-fungal agent terbinafine hydrochloride and the anti-bacterial agents erythromycin and amoxycillin.

In a particular embodiment the composition comprises the anti-fungal agent terbinafine hydrochloride and the anti-bacterial agents clarithromycin and doxycycline.

Typically, the pharmaceutical composition may further include one or more of the following: a mucolytic agent, a steroid, a decongestant and/or a bronchodilator.

Systemic administration may be the oral or parenteral administration of the composition. The composition may be in any form suitable for systemic administration, for example in the form of a capsule, tablet, caplet, solution or suspension.

The present invention further provides for the use of therapeutically effective amounts of at least one anti-fungal agent and two or more anti-bacterial agents for the manufacture of a medicament for systemic administration for the treatment of respiratory tract mucositis.

DETAILED DESCRIPTION OF THE INVENTION

As used herein the term "treatment" refers to any and all uses which remedy a disease state or symptoms, or otherwise prevent, hinder, retard, or reverse the progression of disease or other undesirable symptoms in any way whatsoever. Thus, "treatment" means not only treatment designed to cure or remove symptoms in an individual, but also to ongoing therapy (so-called 'maintenance therapy') designed to control and suppress the occurrence of symptoms. Treatment may be for a defined period of time, or provided on an ongoing basis depending on the particular circumstances of any given individual.

As used herein the term "anti-bacterial agent" refers to any agent that is capable of killing bacteria or is used in the treatment or eradication of infections caused by bacteria. This includes both antibiotics, isolated from natural sources and synthetically generated anti-bacterials.

As used herein the term "emollient" refers to any product applied to the skin which soothes irritation of the skin, including, for example, ointments, liniments, lotions, creams, moisturisers, oils, skin softeners, soaps, shampoo, sunscreens, cosmetics and the like.

As used herein the term "simultaneously" means administration within a 24 hour period. That is, to realise the benefits of the embodiments of the invention it is not necessary that administration of each of the active agents occur at precisely the same time, but rather that the individual receive these agents within a given 24 hour period.

The present invention provides methods and pharmaceutical compositions for treating patients either with acute, chronic, or partially treated respiratory mucositis, in particular asthma, rhinosinusitis, allergic rhinitis, chronic bronchitis, sinusitis, emphysema and cystic fibrosis-associated lung disease. Preferred embodiments of the present invention provide combinations of anti-fungal and anti-bacterial agents which can be used for the effective treatment of deeply seated fungal and bacterial infections which lead to these inflammation states. The anti-bacterial agents used in preferred forms of the present invention are antibiotics or other anti-bacterial agents which are suitable for the eradication of various bacterial infections.

The present invention is based on the discovery by the Applicant that fungal and bacterial infections which are deep in the mucosal cellular structures, can be treated effectively by systemic administration of compositions which include anti-fungal and anti-bacterial agents. Unlike muco-administration of various active agents the systemic therapy of the present invention offers for the first time a viable long term treatment and/or prevention option for sufferers of respiratory tract mucositis.

The present invention teaches compositions and treatments which are contrary to the current understanding of chronic allergic asthma and rhino-sinusitis. Additionally, the present invention provides treatments which avoid surgery for rhino-sinusitis and avoids steroid use which is generally required for asthma treatment.

Administration

Administration of anti-fungal and anti-bacterial agents according to preferred embodiments of the present invention may be by oral, intravenous, intra-arterial, intramuscular, or subcutaneous routes. Typically, administration is by the oral route.

In the methods of the present invention the at least one anti-fungal agent and at least one anti-bacterial agent may be administered in single daily doses, or in two, three, four or more identical or different divided doses per day, and they may be administered simultaneously or at different times during the day. Usually, the active substances will be administered simultaneously. They may be contained in separate medications, or more usually in a single combined dosage form.

Anti-Fungal and Anti-Bacterial Agents

Anti-fungal agents for use according to the methods of the present invention and in compositions of the present invention are preferably selected from the groups consisting of: polyene macrolide, tetrene macrolide, pentaenic macrolide, fluorinated pyrimidine, imidazole, azole, triazole, halogenated phenolic ether, thiocarbamate, allylamine, sterol inhibitor, or an agent that interpolates fungal cell constituents. Preferably the anti-fungal agent is selected from the following group: amphotericin B, flucytosine, ketoconazole, miconazole, itraconazole, fluconazole, griseofulvin, clotrimazole, econazole, terconazole, butoconazole, oxiconazole, sulconazole, supraconazole, voriconazole, ciclopirox olamine, haloprogin, tolnaftate, naftifine, terbinafine hydrochloride, morpholines, nystatin, natamycin, butenafine, undecylenic acid, proprionic acid and caprylic acid. Preferably the anti-fungal agent is selected from the following sub-group: amphotericin B; ketoconazole; fluconazole; and terbinafine hydrochloride.

In combination with the anti-fungal agent or agents this invention includes the co-administration of one or more anti-bacterial agents, preferably being selected from a group consisting of tetracyclines, penicillins, macrolides, quinolones, chloramphenicol, rifamycins, sulphonamides, co-trimoxazole, and oxazolidinones. Examples of these antibiotics include, among others, doxycycline; chlortetracycline; tetracycline hydrochloride; oxytetracycline; demeclocycline; methacycline; minocycline; penicillin; amoxycillin; erythromycin; clarithromycin; roxithromycin; azithromycin; spiramycin; oleandomycin; josamycin; kitsamysin; flurithromycin; nalidixic acid; oxolinic acid; norfloxacin; perfloxacin; amifloxacin; ofloxacin; ciprofloxacin; sparfloxacin; levofloxacin; rifabutin; rifampicin; rifapentin; sulfisoxazole; sulfamethoxazole; sulfadiazine; sulfadoxine; sulfasalazine; sulfaphenazole; dapsone; sulfacytidine; or linezolid as well as other examples of each group of antibiotics enumerated.

In one preferred form the composition of the present invention comprises one anti-fungal and two anti-bacterial agents.

In an alternative form the composition of the present invention comprises two anti-fungal agents and two, three or more anti-bacterial agents.

Preferred Combinations and Dosages

The doses of the anti-fungal agents and anti-bacterial agents used in the pharmaceutical compositions according to preferred forms of the present invention are in accordance with their generally known and established safe dosage ranges when they are used in monotherapy for the treatment of other conditions. Such dosages for anti-bacterial agents are understood by those skilled in the art and generally range from 0.0005 to 50 grams per day, depending on the agent used, as described for example in Martindale, *The Extra Pharmacopoeia,* 31st Edition (The Royal Pharmaceutical Society, London, 1996).

The therapeutically effective amount of anti-fungal and anti-bacterial agents for any particular patient will depend upon a variety of factors including: the disorder being treated and the severity of the disorder; the composition employed; the age, body weight, general health, sex and diet of the patient; the time of administration; the route of administration; the duration of the treatment; drugs used in combination or coincidental with the treatment, together with other related factors well known in medicine.

One skilled in the art would be able, by routine experimentation, to determine an effective, non-toxic amount of the anti-fungal and anti-bacterial agents which would be required to treat the disorders and diseases to which the present application is applicable.

Typically, an effective dose of the appropriate anti-fungal agent(s) and anti-bacterial agent(s) would be expected to be in the range of about 1 milligram (mg) per day to about 4 grams (g) per day, preferably about 10 mg per day to about 2 g per day, even more preferably about 100 mg per day to about 1000 mg per day.

In one preferred embodiment of the method of the present invention there are administered to a patient terbinafine hydrochloride in an amount of 250 mg per day, doxycycline in an amount of 100 mg per day and rifabutin in an amount of 150 mg per day. Preferably administration is oral, twice daily for a period of between one week and six months.

In another preferred method in accordance with the invention, there are administered to a patient terbinafine hydrochloride (250 mg per day), clarithromycin (500 mg per day) and rifampicin (300 mg per day). Preferably administration is oral, twice daily. Such a method of treatment, adjusted to reflect the child's weight, is particularly suitable for administration to children. An alternative effective treatment for children involves the administration of a syrup containing one anti-fungal agent in the form of terbinafine hydrochloride and one anti-bacterial agent in the form of clarithromycin.

In a further preferred method in accordance with the invention there are administered to a patient terbinafine hydrochloride (250 mg per day), doxycycline (100 mg per day) and rifampicin (300 mg per day). Preferably administration is oral, twice daily for a period of two months.

In a further preferred method in accordance with the invention there are administered to a patient terbinafine hydrochloride (250 mg per day), clarithromycin (250 mg per day) and rifabutin (150 mg per day). Preferably administration is oral, twice daily for a period of 1 week to 1 year.

In a further preferred method in accordance with the invention there are administered to a patient terbinafine hydrochloride (250 mg per day), tetracycline hydrochloride (500 mg per day) and rifampicin (300 mg per day). Preferably administration is oral, twice daily for a period of 1 to 3 months.

In a further preferred method in accordance with the invention there are administered to a patient fluconazole (200 mg per day), clarithromycin (500 mg per day) and rifabutin (150 mg per day). Preferably administration is oral, twice daily for a period of 1 to 3 months.

In a further preferred method in accordance with the invention there are administered to a patient terbinafine hydrochloride (250 mg per day), erythromycin (1000 mg per day) and amoxycillin (1000 mg per day). Preferably administration is oral, twice daily.

In a further preferred method in accordance with the invention there are administered to a patient terbinafine hydrochloride (500 mg per day), clarithromycin (500 mg per day) and doxycycline (100 mg per day). Preferably administration is oral, twice daily.

It will be appreciated by those skilled in the art that the dosages provided in the above preferred methods are merely indicative of typical dosages of the specific anti-fungal agents and anti-bacterial agents listed. Actual doses of each active agent administered to any given individual may vary and will depend on a variety of factors including: the disorder being treated and the severity of the disorder; the composition employed; the age, body weight, general health, sex and diet of the individual; the time of administration; the route of administration; the duration of the treatment; drugs used coincidental with the treatment, together with other related factors well known in medicine. For example, dosage amounts higher than those provided in the above preferred methods may be employed in the case of resistant fungal and bacterial infections.

Administration of the relevant composition will be determined on a case by case basis, and may for example be once, twice, three or more times daily. The component medications may be taken simultaneously or separately. The duration of the treatment will depend on the severity and resistance of the underlying condition. Treatment may be prescribed for a duration of one week to one year or more, but typically for two to three months.

Patient response to the treatment may be measured by noting clinical improvement, progressive reduction of reliance upon typical asthma drugs such as steroids and bronchodilators, the improvement in peak flow, and patient well-being and performance.

Pharmaceutical Compositions

One preferred pharmaceutical composition in accordance with the invention comprises terbinafine hydrochloride in an amount of 125 mg, doxycycline in an amount of 50 mg and rifabutin in an amount of 75 mg.

Another preferred pharmaceutical composition in accordance with the invention comprises terbinafine hydrochloride in an amount of 125 mg, clarithromycin in an amount of 250 mg and rifampicin in an amount of 150 mg.

A further preferred pharmaceutical composition in accordance with the invention comprises terbinafine hydrochloride in an amount of 125 mg, doxycycline in an amount of 50 mg and rifampicin in an amount of 150 mg.

Yet another preferred pharmaceutical composition in accordance with the invention comprises terbinafine hydrochloride in an amount of 125 mg, clarithromycin in an amount of 125 mg and rifabutin in an amount of 75 mg.

Yet another preferred pharmaceutical composition in accordance with the invention comprises terbinafine hydrochloride in an amount of 125 mg, tetracycline hydrochloride in an amount of 250 mg and rifampicin in an amount of 150 mg.

Yet another preferred pharmaceutical composition in accordance with the invention comprises fluconazole in an amount of at least 100 mg, clarithromycin in an amount of at least 250 mg and rifabutin in an amount of at least 75 mg.

Yet another preferred pharmaceutical composition in accordance with the invention comprises terbinafine hydrochloride in an amount of 125 mg, erythromycin in an amount of 500 mg and amoxycillin in an amount of 500 mg. Preferably the composition is administered twice daily.

Yet another preferred pharmaceutical composition in accordance with the invention comprises terbinafine hydrochloride in an amount of 250 mg, clarithromycin in an amount of 250 mg and doxycycline in an amount of 50 mg. Preferably the composition is administered twice daily.

A pharmaceutical composition according to the present invention may include one or more pharmaceutically acceptable excipients, adjuvants, diluents or carriers which are generally known in the art.

For oral administration, the pharmaceutical composition may be in the form of tablets, lozenges, pills, troches, capsules, elixirs, powders, including lyophilised powders, solutions, granules, suspensions, emulsions, syrups and tinctures. Slow release, or sustained release forms may also be prepared, for example in the form of coated particles, multi-layer tablets or microgranules. It is preferable for prolonged action that the composition be in a slow or sustained release form.

Solid forms for oral administration may contain pharmaceutically acceptable binders, sweeteners, disintegrating agents, diluents, flavourings, coating agents, preservatives, lubricants and/or time delay agents. Suitable binders include gum acacia, gelatin, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium sterate, steraic acid, sodium oleate, sodium chloride or talc. Suitable time delay agents include glyceryl monosterate or glyceryl disterate.

Liquid forms for oral administration may contain in addition to the active agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further include dispersing agents and/or suspending agents. Suitable suspending agents include sodium carboxymethylcellulose, methylcellulose, hydroxypropylmethyl-cellulose, poly-vinyl-pyrrolidone, sodium alginate or cetyl alcohol. Suitable dispersing agents include lecithin, polyoxyethylene esters of fatty acids such as stearic acid, polyoxyethylene sorbitol mono- or di-oleate, -stearate or laurate, polyoxyethylene sorbitan mono- or di-oleate, -stearate or -laurate and the like.

Pharmaceutical compositions of the present invention may be prepared by blending, grinding, homogenising, suspending, dissolving, emulsifying, dispersing and/or mixing the anti-fungal agent(s) and the anti-bacterial agent(s) together with the selected excipient(s), carrier(s), adjuvant(s) and/or diluent(s). One type of pharmaceutical composition of the present invention in the form of a tablet or capsule may be prepared by (a) preparing a first tablet comprising at least one of the active substances together with any desired excipient(s), carrier(s), adjuvant(s) and/or diluent(s), and (b) preparing a second tablet or a capsule, wherein the second tablet or the capsule includes the remaining active substance(s) and the first tablet. Another type of pharmaceutical composition of the present invention in the form of a capsule may be prepared by (a) preparing a first capsule comprising at least one of the active substances together with any desired excipient(s), carrier(s), adjuvant(s) and/or diluent(s), and (b) preparing a second capsule, wherein the second capsule includes the remaining active substance(s) and the first tablet. A further type of pharmaceutical composition of the present invention in the form of a tablet may be prepared by (a) preparing a capsule comprising at least one of the active substances together with any desired excipient(s), carrier(s), adjuvant(s) and/or diluent(s), and (b) preparing a tablet, wherein the tablet includes the remaining active substance(s) and the capsule.

A pharmaceutical composition of the present invention that comprises at least one anti-fungal agent and at least one anti-bacterial agent may be provided with the active substances contained within a single capsule for monotherapeutic administration. In one form of such a composition, the at least one anti-fungal agent may be contained within an inner capsule or tablet, the inner capsule or tablet being surrounded by the at least one anti-bacterial agent contained within an outer capsule. It will be appreciated that the locations of the components may be reversed such that the at least one anti-bacterial agent may be contained within the inner capsule or tablet and the at least one anti-fungal agent may be contained within the outer capsule. This arrangement will be especially desirable if the active substances are likely to cross-react if contained within the same capsule.

In compositions that comprise three active substances in the form of one anti-fungal agent and two anti-bacterial agents, one active substance may be contained within a central coated tablet or capsule and the remaining two active substances may be contained in an outer capsule in the form of coated microspheres. Other combinations for presentation of the combination of three active substances are possible.

The present invention will now be described by reference to specific Examples, which should not in any way be construed as limiting the scope of the invention. Examples 3 to 5 represent case studies illustrating the effectiveness of preferred embodiments of the treatments and compositions of the present invention.

EXAMPLES

Example 1

A pharmaceutical composition is made with terbinafine hydrochloride, doxycycline and rifampicin in the proportions of 2.5:1:3 by weight, blended and encapsulated into a gelatin capsule, each capsule containing 125 mg terbinafine hydrochloride, 50 mg doxycycline and 150 mg rifampicin.

Example 2

For the treatment of children, a pharmaceutical composition is made with terbinafine hydrochloride, clarithromycin and rifampicin in the proportions of 1:2:1.2 by weight, blended and encapsulated into a gelatin capsule, each capsule containing 125 mg terbinafine hydrochloride, 250 mg clarithromycin and 150 mg rifampicin.

The pharmaceutical composition is self-administered by the patient twice daily for a period of between two months and four months. The progress of the patient may be monitored if desired by measurement of peak flow rates.

Example 3

A 74 year old male with onset of asthma two years prior was chronically treated with standard bronchodilators (Ventolin) and steroid inhalants and intermittent antibiotics. He continued to be symptomatic throughout the treatment with mild to severe episodes.

He was commenced on a combination of terbinafine hydrochloride (250 mg per day), doxycycline (50 mg twice a day), and rifabutin (150 mg per day). After only two weeks of treatment his peakflow meter readings improved twofold and by three months of treatment he had ceased all his steroid and Ventolin therapies. His peakflow meter range reading was at this stage normal for his age. One month later he continued to be totally free of symptoms without any further anti-asthmatic treatment, and at 13 months no further anti-asthma therapy has been required.

Example 4

A 28 year old female with a chronic history of recurrent admissions to hospital and use of oral as well as inhaled steroids and bronchodilators and recurrent use of antibiotics during triggered attacks, was commenced on a combination of terbinafine hydrochloride (250 mg in the morning), clarithromycin (250 mg twice a day), and rifampicin (150 mg twice a day) in the form of a syrup. She was unable to swallow tablets adequately and preferred the syrup which was given bid. Within two weeks of treatment she was able to dispense with all other therapies for asthma and at three months continues well with peakflow readings that are now normal for her age, having previously been severely restricted in her daily activities and work because of recurrent asthma on maximal standard therapies.

Example 5

A 68 year old male with recurrent rhino-sinusitis but without nasal polyps had been treated by an ear nose and throat specialist with various antibiotics over several years. Though the symptoms improved after each course of antibiotics they nevertheless recurred. There was no associated asthma.

The patient was commenced on a course of terbinafine hydrochloride (250 mg per day), doxycycline (50 mg twice a day), and rifampicin (150 mg twice a day) for 2 months. Within 1 week of starting treatment his symptoms disappeared. The patient completed the 2 month course and remains asymptomatic at 14 months and when reviewed at 20 months.

Example 6

A 34 year old obese female with history of severe asthma with steroid dependence and three documented respiratory then cardiac arrests, was commenced on the combination of terbinafine hydrochloride 250 mg twice daily, clarithromycin 250 mg twice daily and doxycycline 50 mg bid. This allowed the patient—after three weeks—to completely remove her steroids which she was using at a dose of 10 mg per day (Prednisone). Her asthma symptoms resolved progressively at about the same time. However she still continued to take Ventolin and Beclomethasone.

Over the following four weeks the patient was able to reduce and then eliminate the use of Ventolin and the Beclomethasone without any day time or nocturnal wheezing. There was no cough as there had been in the past, the patient reported feeling well, indeed much better than she had for many years. However, she developed some nausea and dizziness which was attributed by her local doctor to doxycycline, who then ceased the doxycycline. The patient continued on the clarithromycin 250 mg bd and terbinafine hydrochloride 250 mg bd.

After three months of treatment, the last month of which had been on double therapy not triple, the patient ceased the medication and within three weeks had a recurrence of asthma. Recommencement of the same therapy with higher dose of clarithromycin and doxycycline again controlled the disease and the patient was able to come off all steroids and Ventolin therapy by week four. At this time Doxycycline and Clarithromycin doses were reduced but terbinafine hydrochloride continues at 250 mg bd. The patient did not dare go off the medication for the next six months as she feared developing another cardiac-respiratory arrest.

This Case exemplifies that reduction of dosage or cessation therapy may lead to the possible developing of resistance to antifungal/antibiotic infection, and at the same time exemplifies the concept of maintenance therapy on antibiotics for asthma to completely control the asthma without necessarily eradicating the infection.

The invention claimed is:

1. A pharmaceutical composition for systemic administration for the treatment of the invasive component of fungal or bacterial infection associated with respiratory tract mucositis, said composition comprising therapeutically effective amounts of at least one anti-fungal agent and two or more anti-bacterial agents, wherein said anti-fungal agent is selected from the group consisting of terbinafine hydrochloride and fluconazole, and wherein said two or more anti-bacterial agents are selected from the group consisting of doxycycline, rifabutin, clarithromycin, rifampicin, tetracycline hydrochloride, azithromycin, erythromycin, and amoxycillin.

2. The pharma ceutical composition according to claim 1, wherein the anti-fungal agent is terbinafine hydrochloride and the anti-bacterial agents are doxycycline and rifabutin.

3. The pharma ceutical composition according to claim 1, wherein the anti-fungal agent is terbinafine hydrochloride and the anti-bacterial agents are clarithromycin and rifampicin.

4. The pharma ceutical composition according to claim 1, wherein the anti-fungal agent is terbinafine hydrochloride and the anti-bacterial agents are doxycycline and rifanipicin.

5. The pharma ceutical composition according to claim 1, wherein the anti-fungal agent is terbinafine hydrochloride and the anti-bacterial agents are clarithromycin and rifabutin.

6. The pharma ceutical composition according to claim 1, wherein the anti-fungal agent is terbinafine hydrochloride and the anti-bacterial agents are tetracycline hydrochloride and rifampicin.

7. The pharma ceutical composition according to claim 1, wherein the anti-fungal agent is fluconazole and the anti-bacterial agents are clarithromycin and rifabutin.

8. The pharma ceutical composition according to claim 1, wherein the anti-fungal agent is fluconazole and the anti-bacterial agents are azithromycin and rifampicin.

9. The pharmaceutical composition according to claim 1, wherein the anti-fungal agent is terbinafine hydrochloride and the anti-bacterial agents are azithromycin and rifabutin.

10. The pharma ceutical composition according to claim 1, wherein the anti-fungal agent is terbinafine hydrochloride and the anti-bacterial agents are erythromycin and amoxycillin.

11. The pharma ceutical composition according to claim 1, wherein the anti-fungal agent is terbinafine hydrochloride and the anti-bacterial agents are clarithromycin and doxycycline.

12. The pharma ceutical composition according to claim 1, said composition further including one or more of the following: a mucolytic agent, a steroid, a decongestant and/or a bronchodilator.

13. The pharma ceutical composition according to claim 1, wherein said respiratory tract mucositis is asthma, rhinosinusitis, allergic rhinitis, chronic bronchitis, sinusitis, emphysema or cystic fibrosis-associated lung disease.

14. A pharmaceutical composition for systemic administration for the treatment of the invasive component of fungal or bacterial infection associated with respiratory tract mucositis, said composition comprising therapeutically effective amounts of at least one anti-fungal agent and two or more anti-bacterial agents, wherein said anti-fungal agent is selected from the group consisting of terbinafine hydrochloride and fluconazole, and wherein said two or more anti-bacterial agents belong to one or more of the following classes: macrolides, tetracyclines and rifamycins.

15. The pharmaceutical composition according to claim 14 wherein the anti-bacterial agents are a macrolide and a tetracycline.

16. The pharmaceutical composition according to claim 14 wherein the anti-bacterial agents are a macrolide and a rifamycin.

17. The pharmaceutical composition according to claim 14 wherein the anti-bacterial agents are a tetracycline and a rifamycin.

18. The pharmaceutical composition according to claim 14 wherein the anti-bacterial agents are a macrolide, a tetracycline, and a rifamycin.

* * * * *